(12) United States Patent
Burnside et al.

(10) Patent No.: US 8,206,347 B2
(45) Date of Patent: *Jun. 26, 2012

(54) FEEDING DEVICE INCLUDING BALLOON TIP AND METHOD OF MANUFACTURE

(75) Inventors: Eddie K. Burnside, Grantsville, UT (US); Bret Hamatake, Grantsville, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/902,987

(22) Filed: Oct. 12, 2010

(65) Prior Publication Data

US 2011/0028896 A1    Feb. 3, 2011

Related U.S. Application Data

(62) Division of application No. 11/422,559, filed on Jun. 6, 2006, now Pat. No. 7,819,840.

(60) Provisional application No. 60/687,703, filed on Jun. 6, 2005.

(51) Int. Cl.
*A61J 15/00* (2006.01)
(52) U.S. Cl. .................................. 604/101.01
(58) Field of Classification Search .......... 604/261, 604/910
See application file for complete search history.

(56) References Cited

U.S. PATENT DOCUMENTS

| | | | |
|---|---|---|---|
| 3,915,171 A * | 10/1975 | Shermeta | 604/101.05 |
| 4,177,815 A | 12/1979 | Patel | |
| 4,227,293 A | 10/1980 | Taylor | |
| 4,535,757 A | 8/1985 | Webster, Jr. | |
| 4,606,347 A | 8/1986 | Fogarty et al. | |
| 4,685,901 A | 8/1987 | Parks | |
| 4,701,163 A | 10/1987 | Parks | |
| 4,798,592 A | 1/1989 | Parks | |
| 5,071,405 A | 12/1991 | Piontek et al. | |
| 5,112,310 A | 5/1992 | Grobe | |
| 5,234,454 A | 8/1993 | Bangs | |
| 5,273,529 A | 12/1993 | Idowu | |
| 5,308,325 A | 5/1994 | Quinn et al. | |
| 5,399,173 A | 3/1995 | Parks et al. | |
| 5,429,605 A * | 7/1995 | Richling: Bernd et al. | 604/103.11 |
| 5,439,444 A * | 8/1995 | Andersen et al. | 604/102.02 |
| 5,458,572 A | 10/1995 | Campbell et al. | |

(Continued)

FOREIGN PATENT DOCUMENTS

WO    02087492 A1    11/2002

(Continued)

OTHER PUBLICATIONS

PCT/US2006/022020 filed Jun. 6, 2006 International Preliminary Report on Patentability dated Dec. 6, 2007.

(Continued)

*Primary Examiner* — Christopher D Koharski
*Assistant Examiner* — Diva K Chander
(74) *Attorney, Agent, or Firm* — Rutan & Tucker, LLP

(57) ABSTRACT

A feeding tube device for delivering a substance into a stomach of a patient. The feeding tube may include an overlapping segment integrally formed with and extending from the distal end of the feeding tube, and an inflation lumen defined within the feeding tube. The overlapping segment may surround at least a portion of the distal end of the feeding tube to form a balloon structure in communication with the inflation lumen.

18 Claims, 15 Drawing Sheets

U.S. PATENT DOCUMENTS

| | | | |
|---|---|---|---|
| 5,458,583 | A | 10/1995 | McNeely et al. |
| 5,470,314 | A | 11/1995 | Walinsky |
| 5,522,961 | A | 6/1996 | Leonhardt |
| 5,749,852 | A | 5/1998 | Schwab et al. |
| 5,836,924 | A | 11/1998 | Kelliher et al. |
| 5,993,473 | A | 11/1999 | Chan et al. |
| 5,997,503 | A | 12/1999 | Willis et al. |
| 5,997,546 | A * | 12/1999 | Foster et al. .................. 606/108 |
| 6,066,155 | A | 5/2000 | Amann et al. |
| 6,077,243 | A | 6/2000 | Quinn |
| 6,113,579 | A | 9/2000 | Eidenschink et al. |
| 6,221,042 | B1 | 4/2001 | Adams |
| 6,264,631 | B1 * | 7/2001 | Willis et al. ................ 604/96.01 |
| 6,319,244 | B2 | 11/2001 | Suresh et al. |
| 6,432,080 | B2 | 8/2002 | Pederson, Jr. et al. |
| 6,506,179 | B1 * | 1/2003 | Tiefenthal et al. ....... 604/103.06 |
| 6,595,971 | B1 | 7/2003 | von Dyck et al. |
| 6,858,019 | B2 | 2/2005 | McGuckin, Jr. et al. |
| 6,878,130 | B2 | 4/2005 | Fournie et al. |
| 6,896,665 | B2 | 5/2005 | Picha et al. |
| 6,916,307 | B2 | 7/2005 | Willis et al. |
| 6,960,222 | B2 | 11/2005 | Vo et al. |
| 6,997,909 | B2 | 2/2006 | Goldberg |
| 7,008,438 | B2 | 3/2006 | O'Brien |
| 7,060,050 | B2 | 6/2006 | Kliem et al. |
| 7,124,489 | B2 | 10/2006 | Triebes et al. |
| 7,534,224 | B2 | 5/2009 | Triebes et al. |
| 7,547,303 | B2 | 6/2009 | DeLegge |
| 7,628,775 | B2 | 12/2009 | Adams et al. |
| 7,819,840 | B2 * | 10/2010 | Burnside et al. ......... 604/101.01 |
| 2004/0103518 | A1 | 6/2004 | Triebes et al. |
| 2004/0106899 | A1 * | 6/2004 | McMichael et al. .......... 604/104 |
| 2004/0106901 | A1 | 6/2004 | Letson et al. |
| 2004/0147874 | A1 * | 7/2004 | Kliem et al. ............... 604/96.01 |
| 2005/0038381 | A1 | 2/2005 | McMichael |
| 2005/0267415 | A1 | 12/2005 | Jacques |
| 2006/0276746 | A1 | 12/2006 | Burnside et al. |
| 2007/0021771 | A1 | 1/2007 | Oepen et al. |
| 2007/0088259 | A1 * | 4/2007 | Chu et al. ...................... 604/104 |
| 2007/0255209 | A1 | 11/2007 | Crooms et al. |

FOREIGN PATENT DOCUMENTS

| | | |
|---|---|---|
| WO | 2004050009 A1 | 6/2004 |
| WO | 2007087254 A2 | 8/2007 |

OTHER PUBLICATIONS

PCT/US2006/022020 filed Jun. 6, 2006 Search Report dated Jan. 25, 2007.

PCT/US2006/022020 filed Jun. 6, 2006 Written Opinion dated Jan. 25, 2007.

U.S. Appl. No. 11/422,559, filed Jun. 6, 2006 Final Office Action dated Apr. 2, 2009.

U.S. Appl. No. 11/422,559, filed Jun. 6, 2006 Non-Final Office Action dated Aug. 8, 2008.

U.S. Appl. No. 11/422,559, filed Jun. 6, 2006 Non-Final Office Action dated Jan. 6, 2010.

U.S. Appl. No. 11/422,559, filed Jun. 6, 2006 Notice of Allowance dated Jun. 24, 2010.

U.S. Appl. No. 11/738,979, filed Apr. 23, 2007 Advisory Action dated Jun. 18, 2009.

U.S. Appl. No. 11/738,979, filed Apr. 23, 2007 Final Office Action dated Apr. 16, 2009.

U.S. Appl. No. 11/738,979, filed Apr. 23, 2007 Final Office Action dated Jan. 25, 2010.

U.S. Appl. No. 11/738,979, filed Apr. 23, 2007 Non-Final Office Action dated Nov. 24, 2008.

U.S. Appl. No. 11/738,979, filed Apr. 23, 2007 Non-Final Office Action dated Oct. 9, 2009.

* cited by examiner

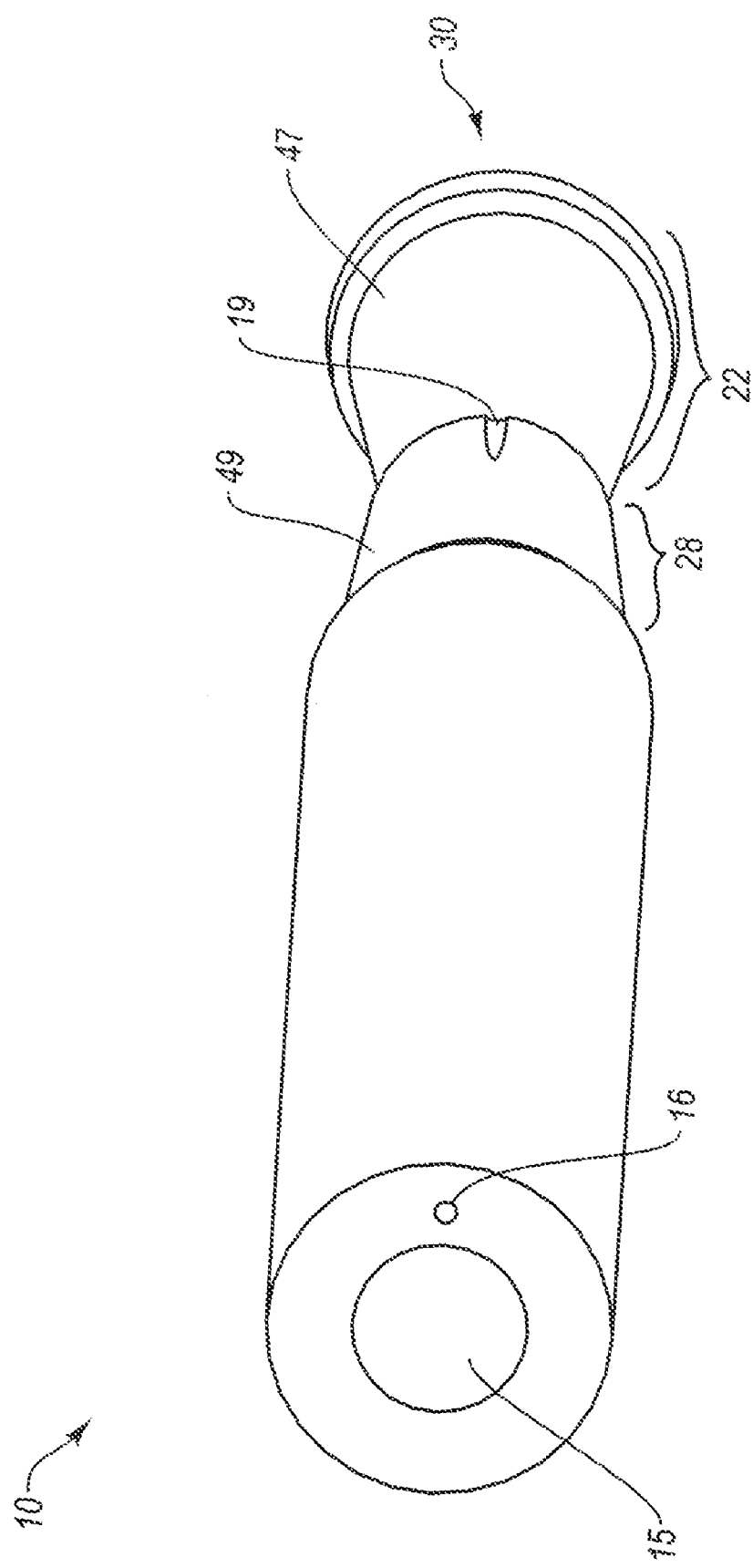

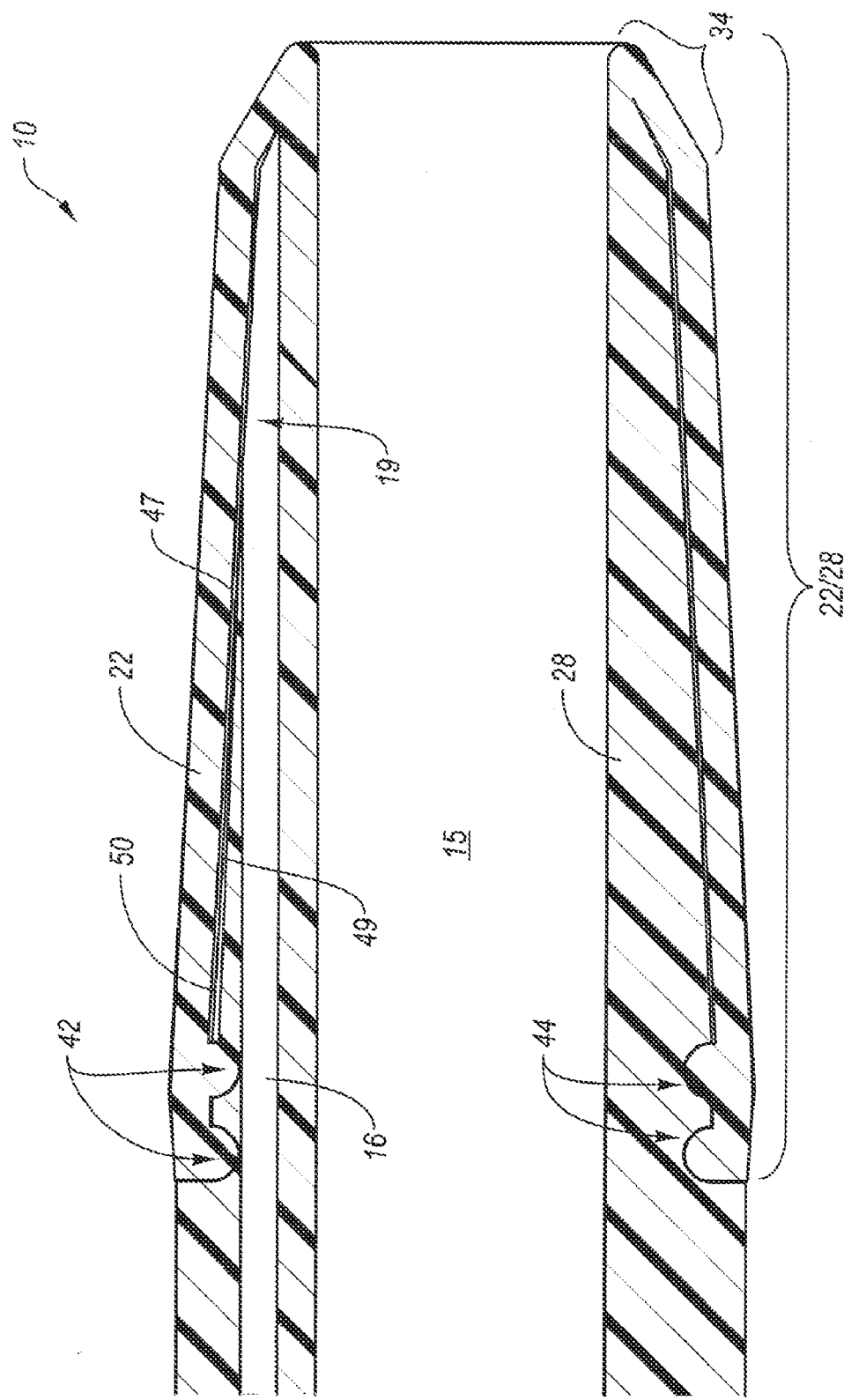

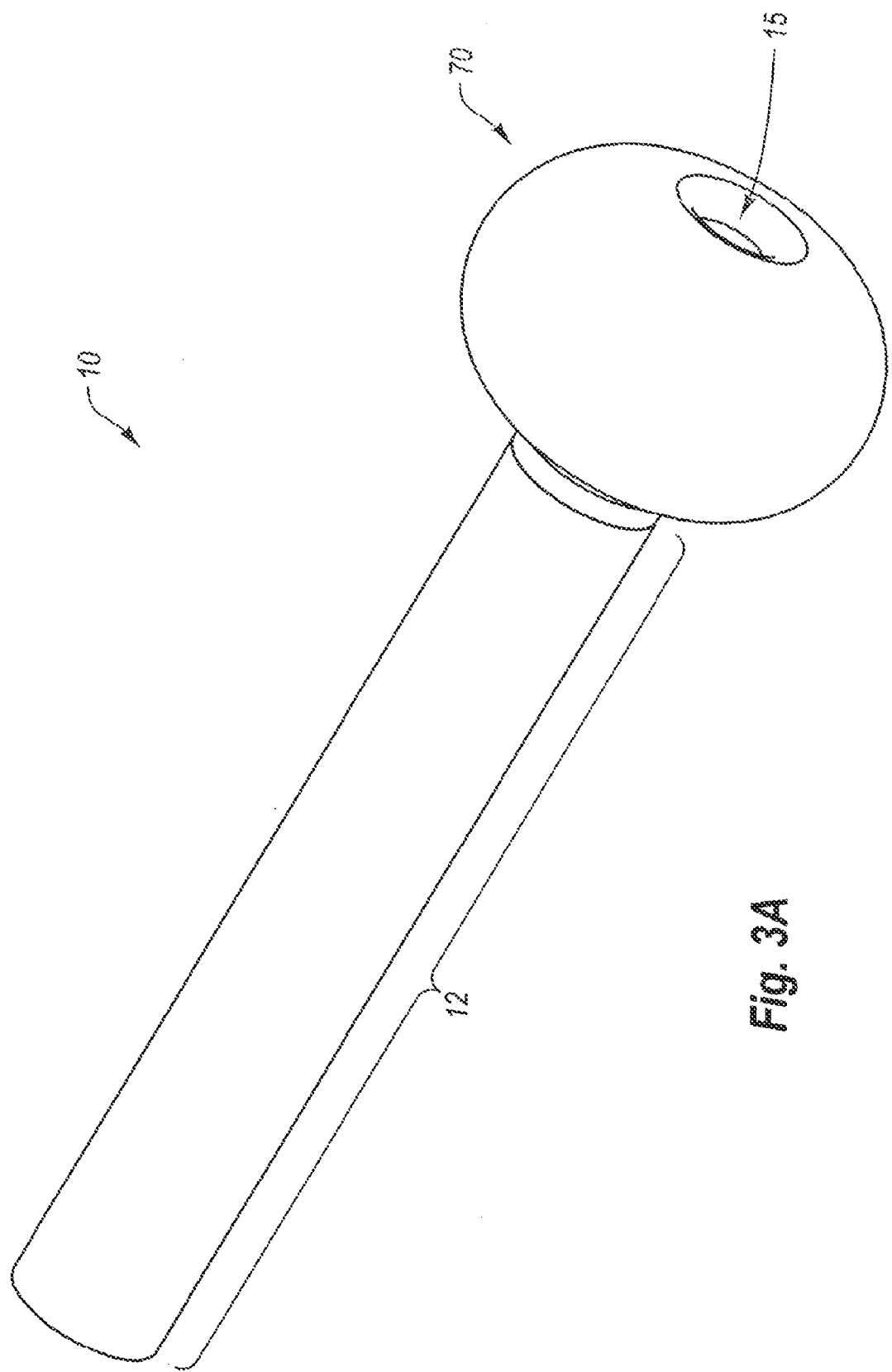

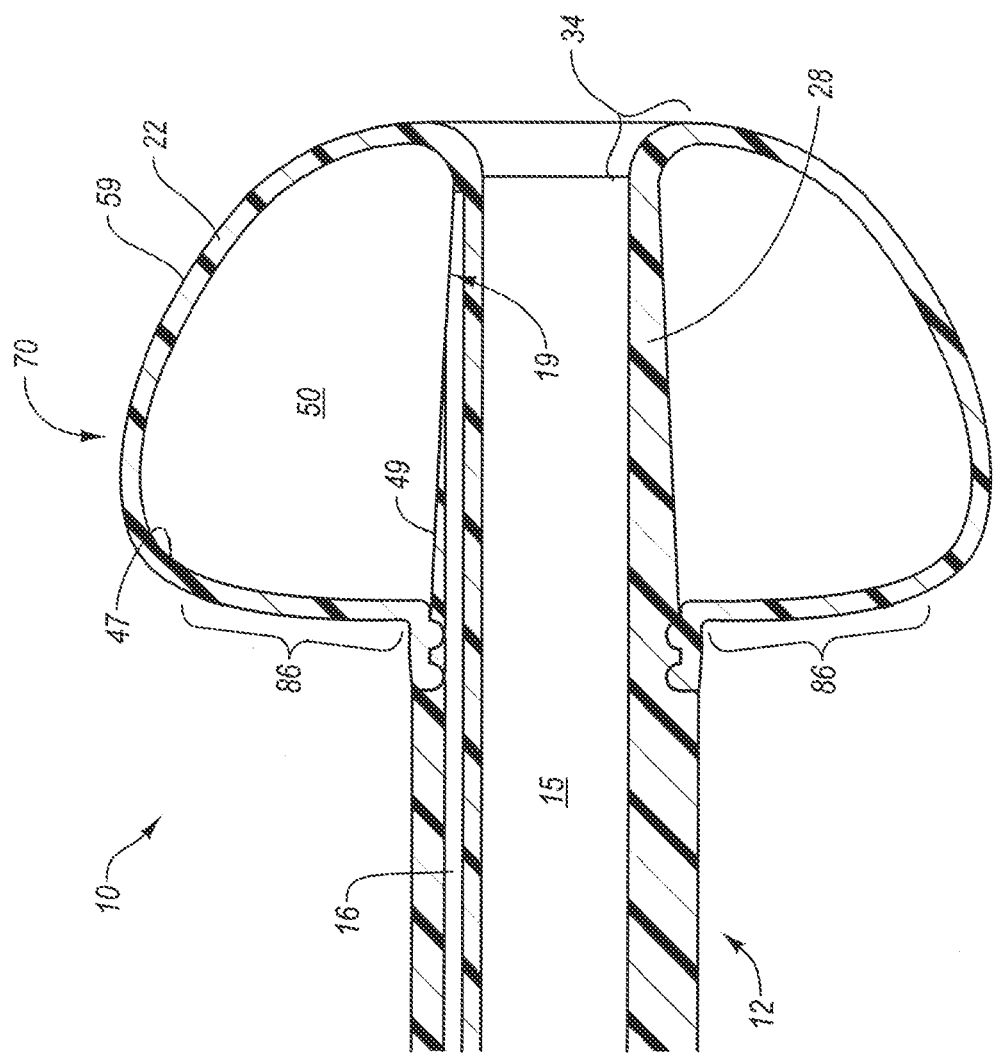

FEEDING DEVICE INCLUDING BALLOON TIP AND METHOD OF MANUFACTURE

PRIORITY

This application is a division of U.S. patent application Ser. No. 11/422,559, filed Jun. 6, 2006, now U.S. Pat. No. 7,819,840, which claims priority to U.S. Provisional Patent Application No. 60/687,703, filed Jun. 6, 2005, each of which is incorporated by reference into this application as if fully set forth herein.

BACKGROUND OF THE INVENTION

Tube feeding may be necessary when a patient requires long-term feeding assistance. A feeding tube is typically placed within the stomach of a patient by inserting the feeding tube through an incision made through a patient's abdominal and stomach walls. Such a process may be generally referred to as a "gastrostomy." A nutrient solution may then be introduced through the feeding tube or gastrostomy tube and into the stomach for providing long-term feeding of the patient. Methods for placing the feeding tube, as well as specifications and techniques for removing the feeding tube, vary. One type of conventional feeding tube comprises a balloon for positioning and retaining the feeding tube within the incision.

SUMMARY

In at least one embodiment, a feeding tube device for delivering a substance into a stomach of a patient comprises a feeding tube having a proximate end and a distal end, an overlapping segment integrally formed with and extending from the distal end of the feeding tube, and an inflation lumen defined within at least a portion of the feeding tube. The overlapping segment may be configured to at least partially surround at least a portion of the distal end of the feeding tube to form a balloon structure in fluid communication with the inflation lumen.

In certain embodiments, the distal end of the feeding tube may further comprise a receiving surface and the overlapping segment may comprise a sealing surface configured to seal against at least a portion of the receiving surface of the distal end of the feeding tube device. The sealing surface may also comprise at least one coupling structure and the receiving surface may comprise at least one coupling recess configured to receive the at least one coupling structure. In some embodiments, at least a portion of the sealing surface may be affixed to at least a portion of the receiving surface. In an additional embodiment, at least a portion of the sealing surface may be compressed against at least a portion of the receiving surface.

According to some embodiments, the overlapping segment may comprise a plurality of circumferential rib structures. In addition, the distal end of the feeding tube may be formed in any number of shapes and sizes, such as a substantially frustoconical or tapered shape. The overlapping segment may also be formed of any number or combination of materials, such as a substantially non-pliant material. In at least one embodiment, the balloon structure may extend beyond the distal end of the feeding tube device when the balloon structure is inflated. In certain embodiments, the feeding tube and the overlapping segment integrally formed with and extending from the distal end of the feeding tube may both be formed of the same material or combination of materials.

In at least one embodiment, the feeding tube device may further comprise a second overlapping segment integrally formed with and extending from the proximate end of the feeding tube. This second overlapping segment may be configured to at least partially surround at least a portion of the proximate end of the feeding tube to form a second balloon structure, which second balloon structure may be in communication with a second inflation lumen defined within at least a portion of the feeding tube.

In at least one embodiment, a method of manufacturing a feeding tube device comprises providing a feeding tube having a proximate end, a distal end, an exterior surface, and an interior surface, providing an overlapping segment integrally formed with and extending from the distal end of the feeding tube, with the overlapping segment comprising an exterior surface and an interior surface, defining an inflation lumen within at least a portion of the feeding tube, disposing the overlapping segment around at least a portion of the distal end of the feeding tube, and sealing at least a portion of the exterior surface of the overlapping segment to the exterior surface of the distal end of the feeding tube to form a balloon structure in fluid communication with the inflation lumen. In certain embodiments, the method may further comprise affixing at least a portion of the exterior surface of the overlapping segment to the exterior surface of the distal end of the feeding tube. Optionally, the method may further comprise compressing at least a portion of the overlapping segment against at least a portion of the distal end of the feeding tube.

According to certain embodiments, a gastric feeding tube device may comprise a feeding tube having a proximate end, a distal end, an exterior surface, and an interior surface, an overlapping segment integrally formed with and extending from the distal end of the feeding tube, with the overlapping segment comprising an exterior surface and an interior surface, and an inflation lumen defined within at least a portion of the feeding tube. In at least one embodiment, the overlapping segment may be configured to at least partially surround at least a portion of the distal end of the feeding tube, with at least a portion of the exterior surface of the overlapping segment sealed against at least a portion of the exterior surface of the distal end of the feeding tube to form a balloon structure. The balloon structure may also be in fluid communication with the inflation lumen and extend beyond the distal end of the feeding tube device when the balloon structure is inflated.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

FIG. 1B is an additional perspective view of the exemplary feeding tube device illustrated in FIG. 1A;

FIG. 2B is an enlarged cross-sectional side view of the exemplary feeding tube device illustrated in FIG. 2A;

FIG. 3A is a perspective view of the exemplary feeding tube device illustrated in FIG. 1A in a third, expanded position;

FIG. 6B is a schematic cross-sectional side view of an exemplary feeding tube device according to an additional embodiment;

Figure 1A:
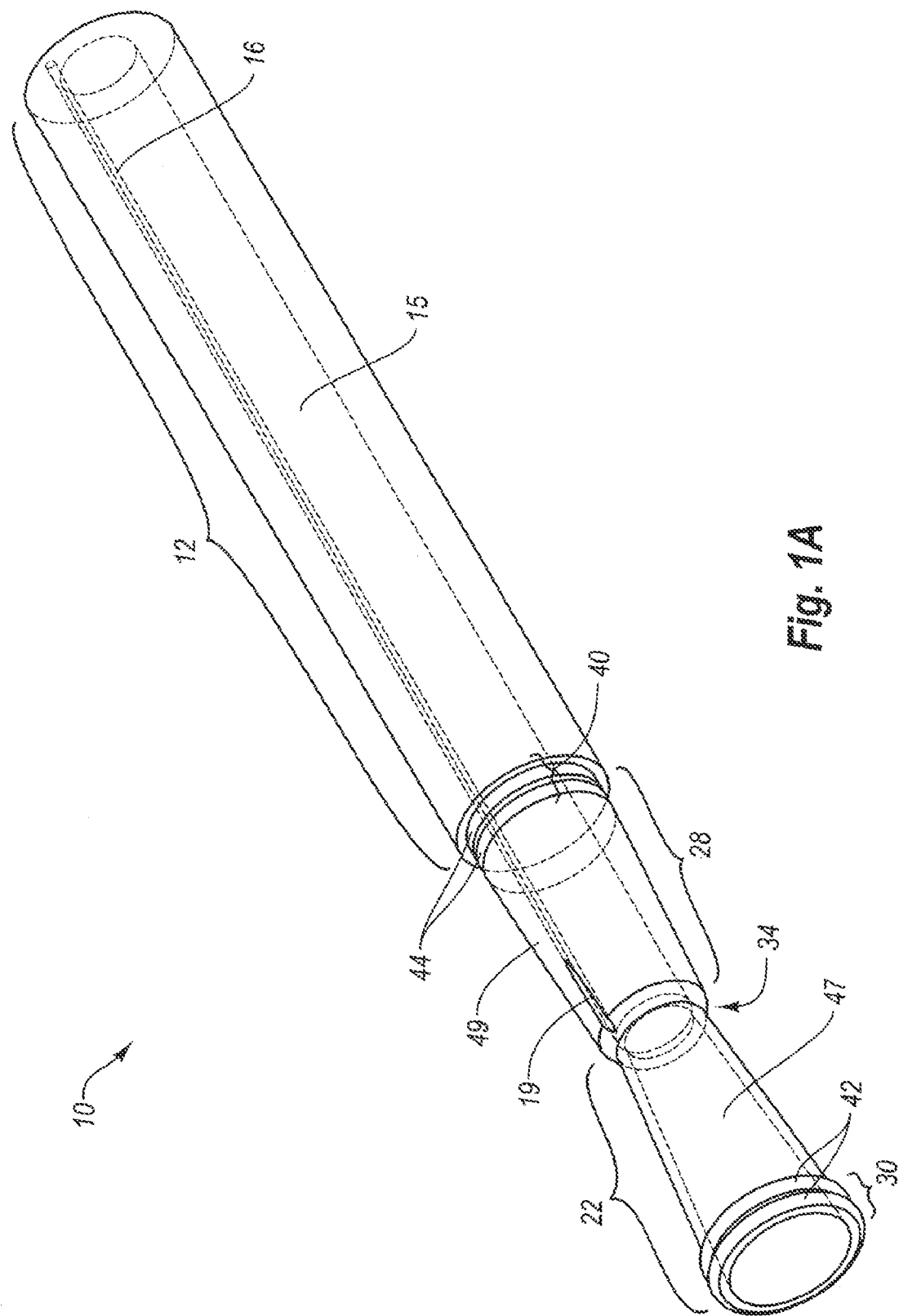
FIG. 1A is a schematic, perspective view of an exemplary feeding tube device in a first position.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, one of skill in the art will understand that the exemplary embodiments described herein are not intended to be limited to the particular forms disclosed. Rather, the instant disclosure covers all modifications, equivalents, and alternatives falling within the scope defined by the appended claims.

DETAILED DESCRIPTION OF EXEMPLARY EMBODIMENTS

Figure 1C:
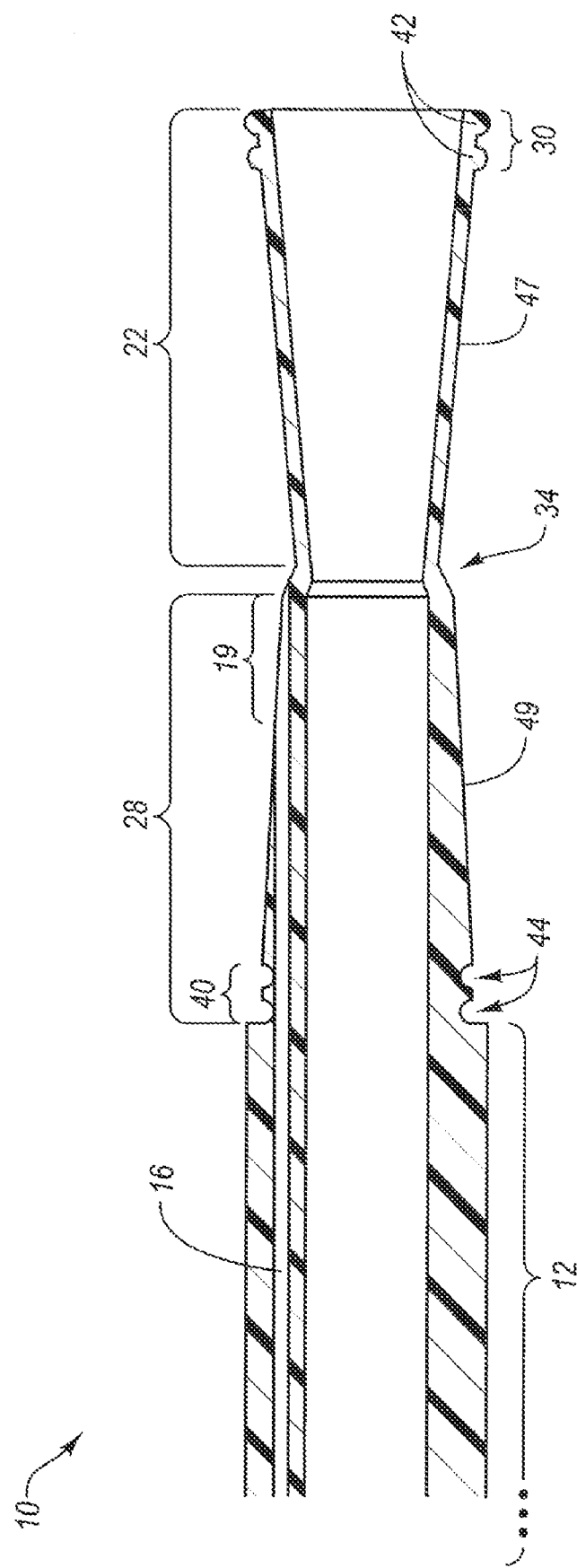
FIG. 1C is a partial cross-sectional side view of the exemplary feeding tube device illustrated in FIG. 1A.

FIGS. 1A-1C are perspective and cross-sectional views of an exemplary feeding tube device 10 according to at least one embodiment. Feeding tube device 10 generally represents any structure or device capable of providing a substance, such as a nutrient solution or a medication, into the stomach of a patient. Generally speaking, feeding tube device 10 may comprise any material exhibiting suitable biocompatibility and mechanical characteristics. For example, feeding tube device 10 may comprise a pliant, resilient material, such as silicone, latex, rubber, or the like.

In at least one embodiment, as seen in FIGS. 1A-1C, exemplary feeding tube device 10 comprises a substantially cylindrical body region 12, a tip region 28 extending longitudinally from a distal end of body region 12, and an overlapping segment 22 extending longitudinally from tip region 28. As shown in FIG. 1C, overlapping segment. 22 may be integrally formed with tip region 28 of feeding tube device 10. Similarly, in certain embodiments, tip region 28 may be integrally formed with body region 12. "Integrally," as used herein, generally means monolithic, continuous, or of a one-piece construction. Thus, in certain embodiments, tip region 28 and overlapping segment 22 may extend from body region 12 of feeding tube device 10 without any joints or seams. In an additional embodiment, overlapping segment 22 may be adhered to an interior surface of tip region 28.

In general, tip region 28 and overlapping segment 22 may be formed in any number of shapes and sizes. For example, in the exemplary embodiments illustrated in FIGS. 1A-1C, tip region 28 may be substantially frustoconical in shape. In other words, the outer diameter of tip region 28 may gradually decrease as tip region 28 extends towards overlapping segment 22. Similarly, the outer diameter of overlapping segment 22 may gradually increase as segment 22 extends away from tip region 28. As explained in greater detail below, the substantially frustoconical shape of tip region 28 and overlapping segment 22 may decrease the amount of force required to insert feeding tube device 10 into a gastric fistula or gastroma.

The various components of feeding tube device 10 (e.g., body region 12, tip region 28, and overlapping segment 22) may also comprise any number or combination of materials. For example, in certain embodiments, body region 12, tip region 28, and/or overlapping segment 22 may comprise a pliant, resilient material, such as silicone, latex, rubber, or the like. In an additional embodiment, discussed in greater detail below, body region 12, tip region 28, and/or overlapping segment 22 may comprise a polymer, such as polyethylene terephthalate (PET), polyurethane, polyethylene (PE), nylon, polyvinyl chloride (PVC), or the like. In at least one embodiment, body region 12, tip region 28, and overlapping segment 22 may each be formed of the same material or combination of materials. Optionally, overlapping segment 22 may be formed from a material or combination of materials that differ from the material or combination of materials used to form body region 12 and tip region 28. In many embodiments, overlapping segment 22 comprises a pliant material suitable for repeated expansion and contraction, as discussed in further detail below.

As seen in the exemplary embodiments illustrated in FIGS. 1A-1C, a flexible region 34 may be disposed between overlapping segment 22 and tip region 28. Flexible region 34 generally represents any structure or material capable of bending or flexing. In at least one embodiment, flexible region 34 may be integrally formed with both tip region 28 and overlapping segment 22. In an additional embodiment, flexible region 34 may be formed by bending a portion of the material joining overlapping segment 22 with tip region 28. As will be discussed in greater detail below in connection with FIGS. 2A-2B, overlapping segment 22 may be folded backwards and disposed or positioned over and around at least a portion of tip region 28 by bending or flexing flexible region 34.

In certain embodiments, one or more lumens may be defined within feeding tube device 10. For example, in the exemplary embodiments illustrated in FIGS. 1A-1C, a substance delivery lumen 15 may be defined within and extend through at least a portion of body region 12, tip region 28, and overlapping segment 22 of feeding device 10. Substance delivery lumen 15 may be configured to deliver a substance, such as a nutrient solution or a medication, through feeding tube device 10 and into the stomach of a patient. In addition, a balloon inflation lumen 16 may be defined within and extend through body region 12 and at least a portion of tip region 28. In at least one embodiment, inflation lumen 16 may be sized and positioned to communicate a fluid, such as a gas, a liquid, or mixtures thereof, through body region 12 and tip region 28 and out of an aperture 19 defined within tip region 28, as will be discussed in greater detail below.

Figure 2A:
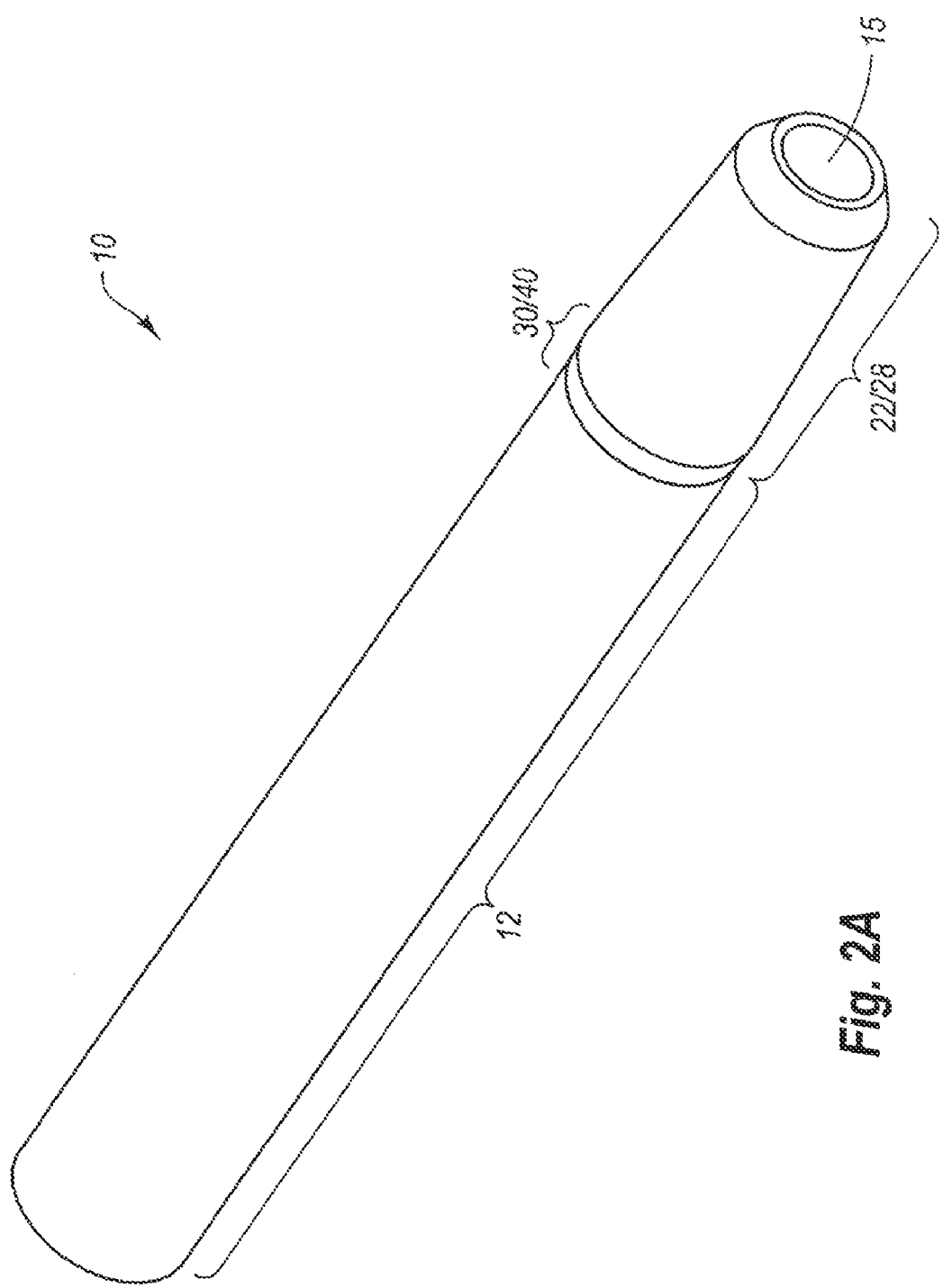
FIG. 2A is a perspective view of the exemplary feeding tube device illustrated in FIG. 1A in a second, overlapped position.

As detailed above, and as illustrated in FIGS. 2A and 2B, overlapping segment 22 may be folded backwards and disposed or positioned over and around at least a portion of tip region 28. In at least one embodiment, at least a portion of an exterior surface 47 of overlapping segment 22 may be affixed to at least a portion of an exterior surface 49 of tip region 28. For example, overlapping segment 22 may comprise a sealing surface 30 that may be adhered, bonded, or otherwise affixed to a receiving surface 40 of tip region 28. In general, sealing surface 30 and receiving surface 40 may be formed in any number of shapes and sizes. For example, as illustrated in FIGS. 1A-1C, sealing surface 30 of overlapping segment 22 may comprise at least one coupling structure 42. Similarly, receiving surface 40 of tip region 28 may comprise at least one coupling recess 44 configured to receive coupling structure 42. Coupling structure 42 and coupling recess 44 generally represent any type of structure (e.g., a protrusion) or recess capable of coupling overlapping segment 22 to tip region 28. For example, the at least one coupling structure 42 and the at least one coupling recess 44 may be configured to engage, touch, or otherwise fit against each other upon folding or positioning the exterior surface 47 of overlapping segment 22 proximate to the exterior surface 49 of tip region 28. In certain embodiments, coupling structure 42 may be adhered, bonded, or otherwise affixed to the outer surface of coupling recess 44.

FIGS. 2A and 2B are perspective and cross-sectional views of the exemplary feeding tube device 10 illustrated in FIG. 1A in a second, overlapped position. As seen in these figures, and as detailed above, overlapping segment 22 may be folded backwards and disposed or positioned over and around at least a portion of tip region 28. In at least one embodiment, a chamber 50 may be formed between the exterior surface 47 of overlapping segment 22 and the exterior surface 49 of tip region 28 by melting, adhering, bonding, sealing, or otherwise affixing at least a portion of sealing surface 30 of overlapping segment 22 to receiving surface 40 of tip region 28. As seen in FIG. 2B, chamber 50 may be in communication (e.g., pneumatic or hydraulic communication) with inflation lumen 16 via aperture 19. As explained in greater detail below in connection with FIGS. 3A-3B, in certain embodiments, at least a portion of overlapping segment 22 may be expanded by communicating a fluid or gas through inflation lumen 16, out aperture 19, and into chamber 50.

As illustrated in FIGS. 2A and 2B, when overlapping segment 22 is folded backwards and disposed around tip region 28, flexible region 34 may exhibit a substantially tapered shape. In certain embodiments, the tapered shape of flexible region 34 may reduce the amount of force required to insert feeding tube device 10 through an incision in a patient's stomach and/or abdominal wall. The tapered shape of flexible region 34 may also ameliorate or prevent trauma to the patient's abdominal and/or stomach walls as feeding tube device 10 is inserted into or removed from the patient's stomach.

Figure 3B:
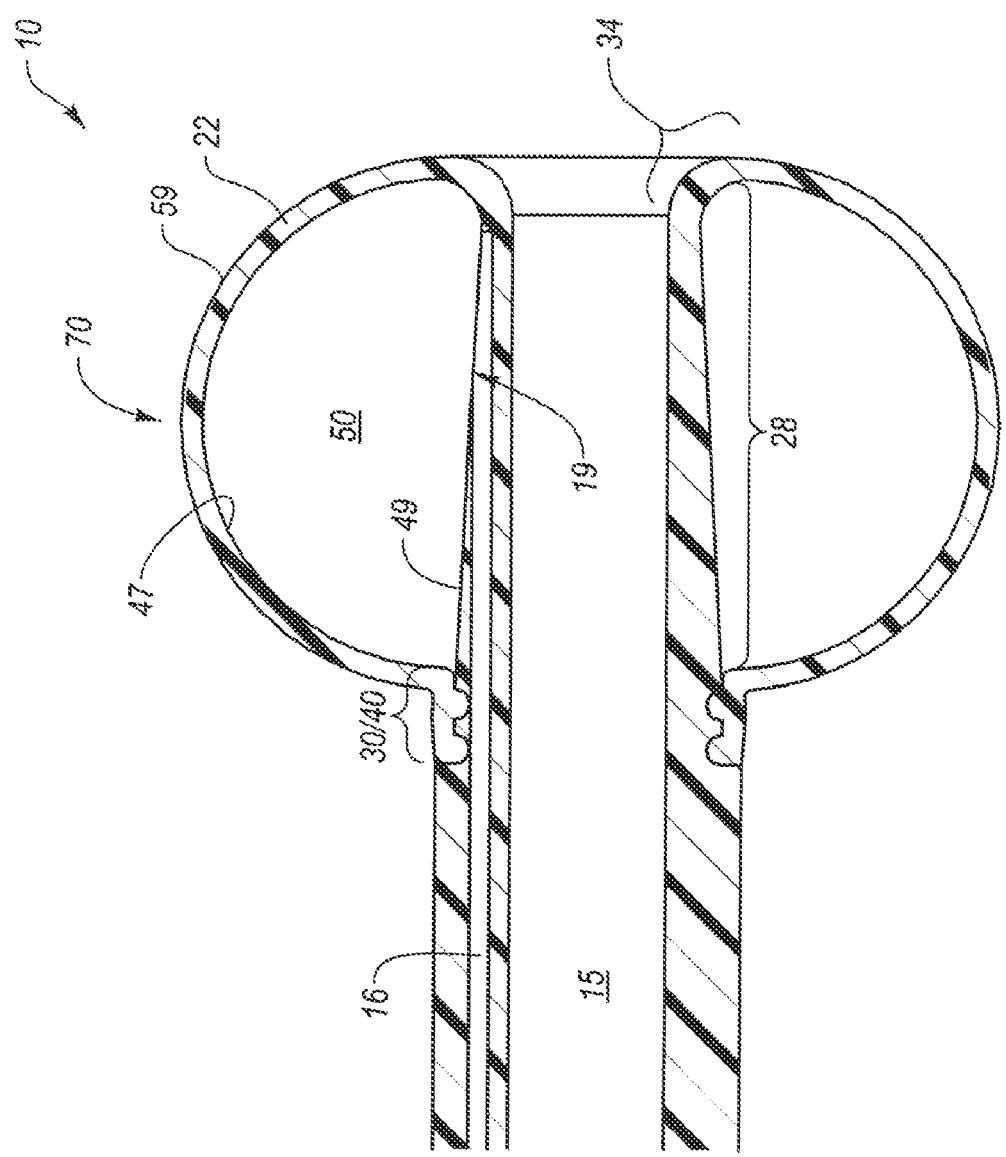
FIG. 3B is an enlarged cross-sectional side view of the exemplary feeding tube device illustrated in FIG. 3A.

FIGS. 3A-3B are perspective and cross-sectional views of the exemplary feeding tube device 10 illustrated in FIG. 1A in a third, expanded position. As seen in these figures, in certain embodiments at least a portion of overlapping segment 22 may be expanded to form a balloon structure 70 by communicating a fluid or gas through inflation lumen 16, out aperture 19, and into chamber 50. Balloon structure 70 generally represents any structure formed by expanding at least a portion of overlapping segment 22. In many embodiments, balloon structure 70 may be sized and configured for positioning and retaining feeding tube device 10 within a gastric fistula or gastroma. As discussed in greater detail below, balloon structure 70 may be formed in any number of shapes and sizes.

In at least one embodiment, after overlapping segment 22 has been expanded to form balloon structure 70 by communicating a fluid or gas into chamber 50, inflation lumen 16 may be sealed to maintain a desired size and/or shape of balloon structure 70. In addition, overlapping segment 22 may be contracted and the size of balloon structure 70 reduced by removing the fluid or gas within chamber 50 via inflation lumen 16. In certain embodiments, all of the fluid or gas within chamber 50 may be removed to fully contract overlapping segment 22 so that feeding tube device 10 may be removed from a patient. In an additional embodiment, overlapping segment 22 may only be partially contracted by removing only a portion of the fluid or gas within chamber 50 so that a user of feeding tube device 10 may reposition or otherwise adjust the location of feeding tube device 10.

Exemplary feeding tube device 10 may provide several advantages over devices in the prior art. For example, in certain embodiments the integral construction of the various elements in feeding tube device 10 may: 1) reduce or eliminate the potential of joint or seam failure; 2) reduce manufacturing costs and the overall complexity of the device; and/or 3) reduce the overall diameter of the feeding tube device 10 by eliminating the need for joints and seams. In addition, in many embodiments the tapered shape of flexible region 34 may reduce the amount of force required to insert feeding tube device 10 through an incision in a patient's stomach and/or abdominal wall, thereby ameliorating or preventing trauma to the patient's abdominal and/or stomach walls. Moreover, because, as illustrated in FIGS. 3A-3B, balloon structure 70 may expand beyond and effectively surround the tapered end of flexible region 34, balloon structure 70 may help prevent the tapered end of flexible region 34 from contacting the backside of a patient's stomach wall, thus preventing potential trauma to the patient's stomach wall.

Figure 4A:
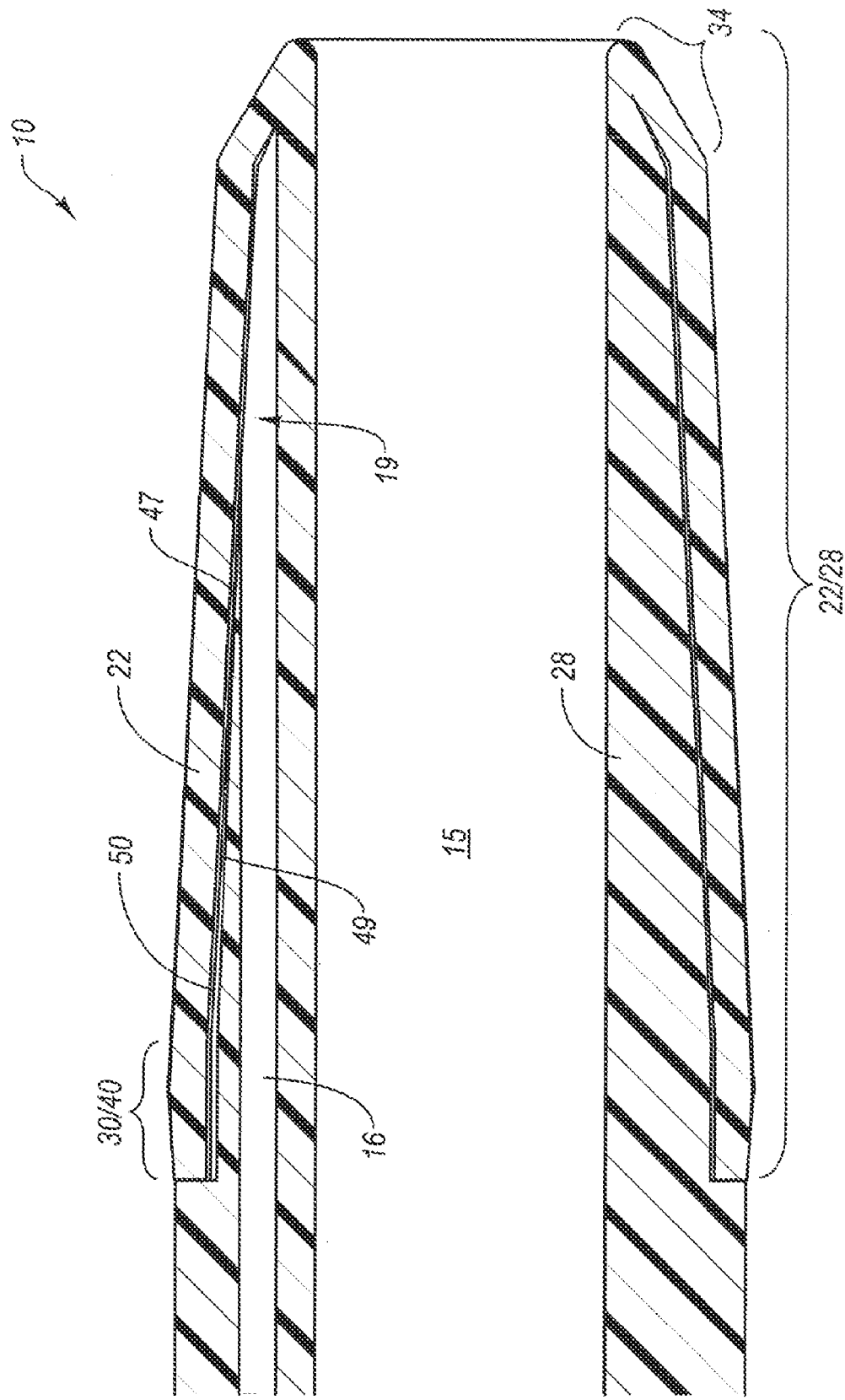
FIG. 4A is an enlarged cross-sectional side view of an exemplary feeding tube device according to an additional embodiment.

The preceding description has been provided to enable others skilled in the art to best utilize various aspects of the exemplary embodiments described herein. This exemplary description is not intended to be exhaustive or to be limited to any precise form disclosed. Many modifications and variations are possible without departing from the spirit and scope of the instant disclosure. For example, as detailed above, sealing surface 30 of overlapping segment 22 and receiving surface 40 of tip region 28 may be formed in any number of shapes and sizes. In particular, as shown in the cross-sectional side view of FIG. 4A, sealing surface 30 and receiving surface 40 may be substantially planar or smooth, as opposed to respectively comprising one or more coupling structures and coupling recesses. In addition, sealing surface 30 and receiving surface 40 may also each comprise substantially cylindrical surfaces or may each be at least partially conical or tapered.

Figure 4B:
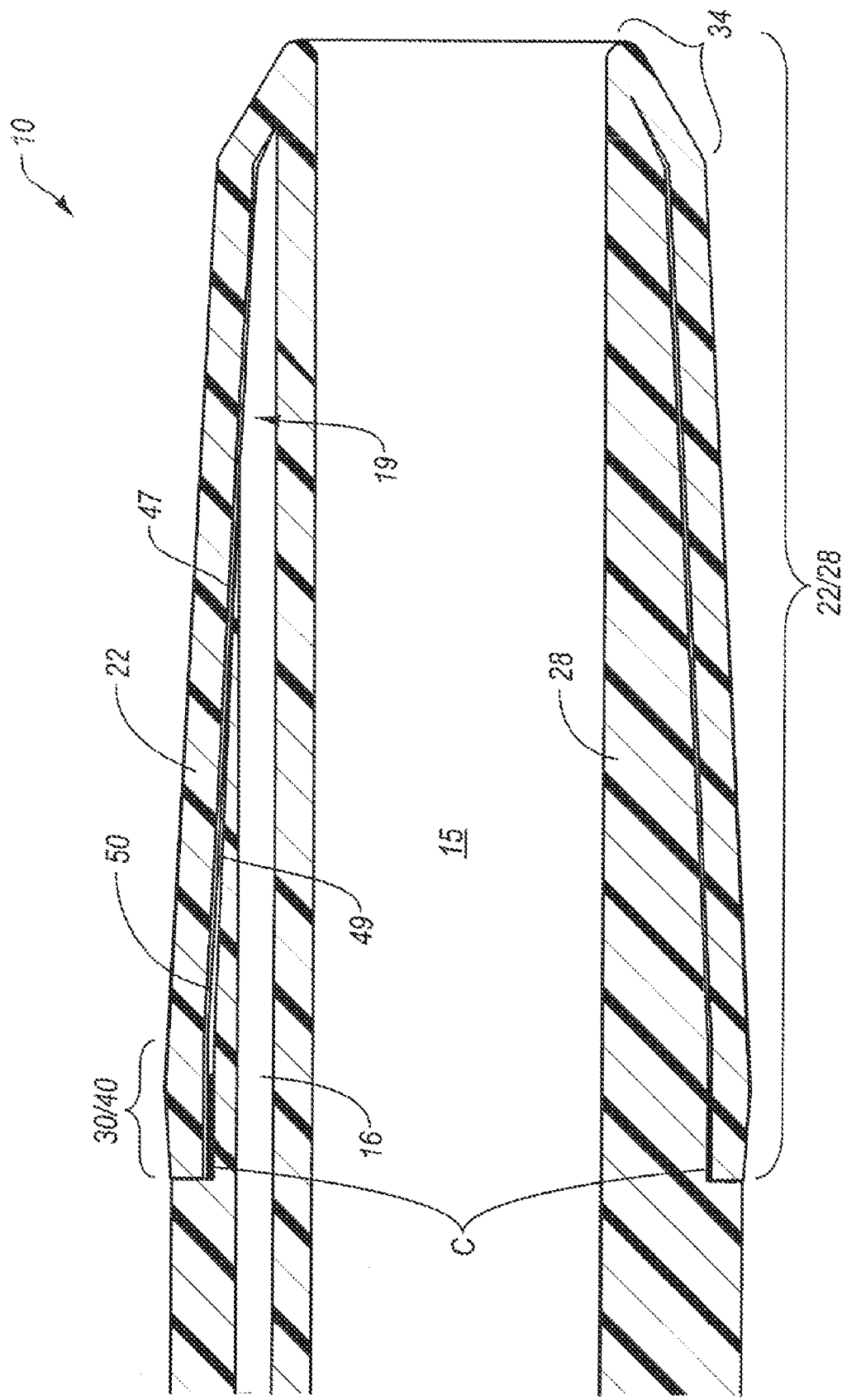
FIG. 4B is an enlarged cross-sectional side view of an exemplary feeding tube device according to an additional embodiment.

In addition, as illustrated in the cross-sectional side view of FIG. 4B, at least a portion of sealing surface 30 of overlapping segment 22 (generally labeled as region "C" in FIG. 4B) may be compressed against receiving surface 40 of tip region 28. In one embodiment, sealing surface 30 may be compressed against receiving surface 40 by configuring at least a portion of overlapping segment 22 (e.g., sealing surface 30) to have an undeformed outer diameter that is smaller than an undeformed outer diameter of at least a portion of tip region 28 (e.g., receiving surface 40). Thus, when overlapping segment 22 is folded backwards and disposed or positioned over and around at least a portion of tip region 28, the smaller receiving surface 30 of overlapping segment 22 may contract around and against the larger receiving surface 40 of tip region 28 to seal chamber 50. In certain embodiments, sealing surface 30 and receiving surface 40 may be sized so that the compressive sealed engagement between these two surfaces provides a seal sufficient to maintain an expected pressure within chamber 50. In an additional embodiment, overlapping segment 22 may be compressed against tip region 28 by an external biasing element, such as an elastic ring or similar element.

Figure 5A:
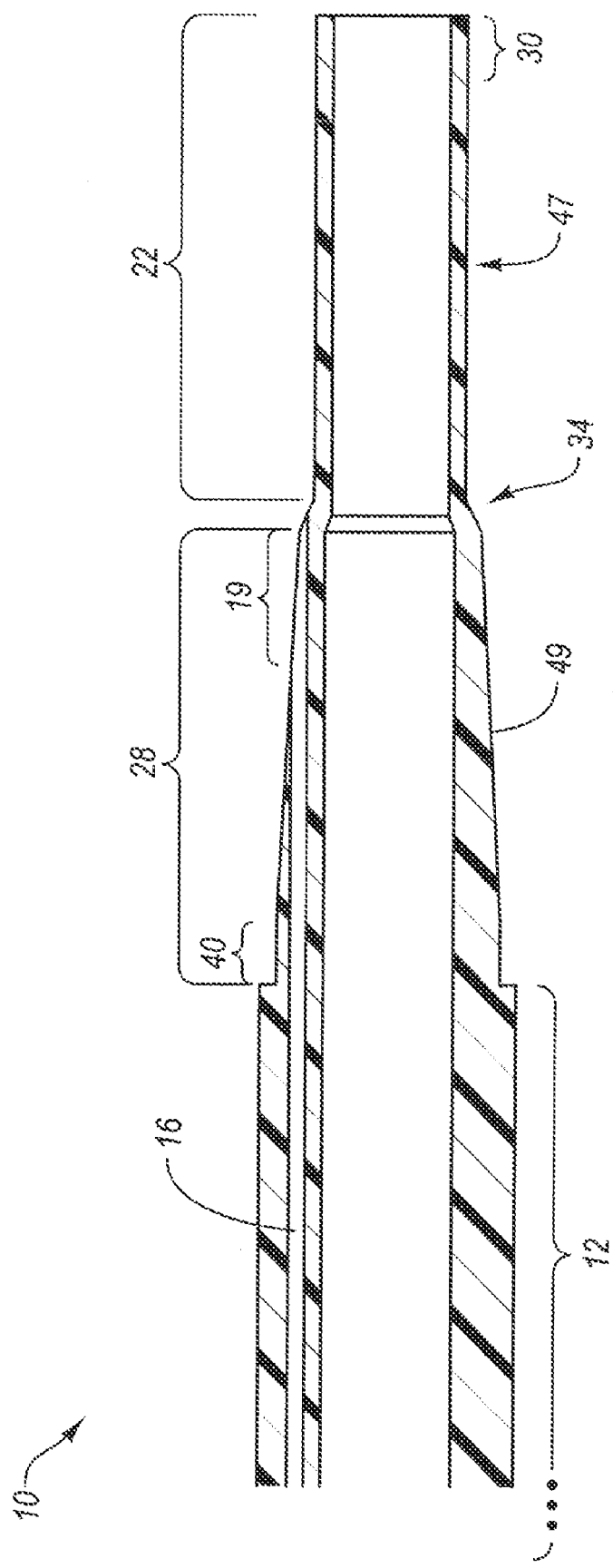
FIG. 5A is an enlarged cross-sectional side view of an exemplary feeding tube device according to an additional embodiment.

FIG. 5A is an enlarged cross-sectional side view of an exemplary feeding tube device 10 according to an additional embodiment. As seen in this figure, exemplary feeding tube device 10 may comprise a substantially cylindrical body region 12, a tip region 28 extending longitudinally from body region 12, and an overlapping segment 22 extending longitudinally from tip region 28. In certain embodiments, overlapping segment 22 may have a substantially constant cross-section, as opposed to tapering or exhibiting a substantially frustoconical shape. In addition, although tip region 28 is illustrated in FIG. 5A as being tapered or substantially frustoconical in shape, tip region 28 may also, similar to overlapping segment 22 in FIG. 5A, have a constant cross-section.

Figure 5B:
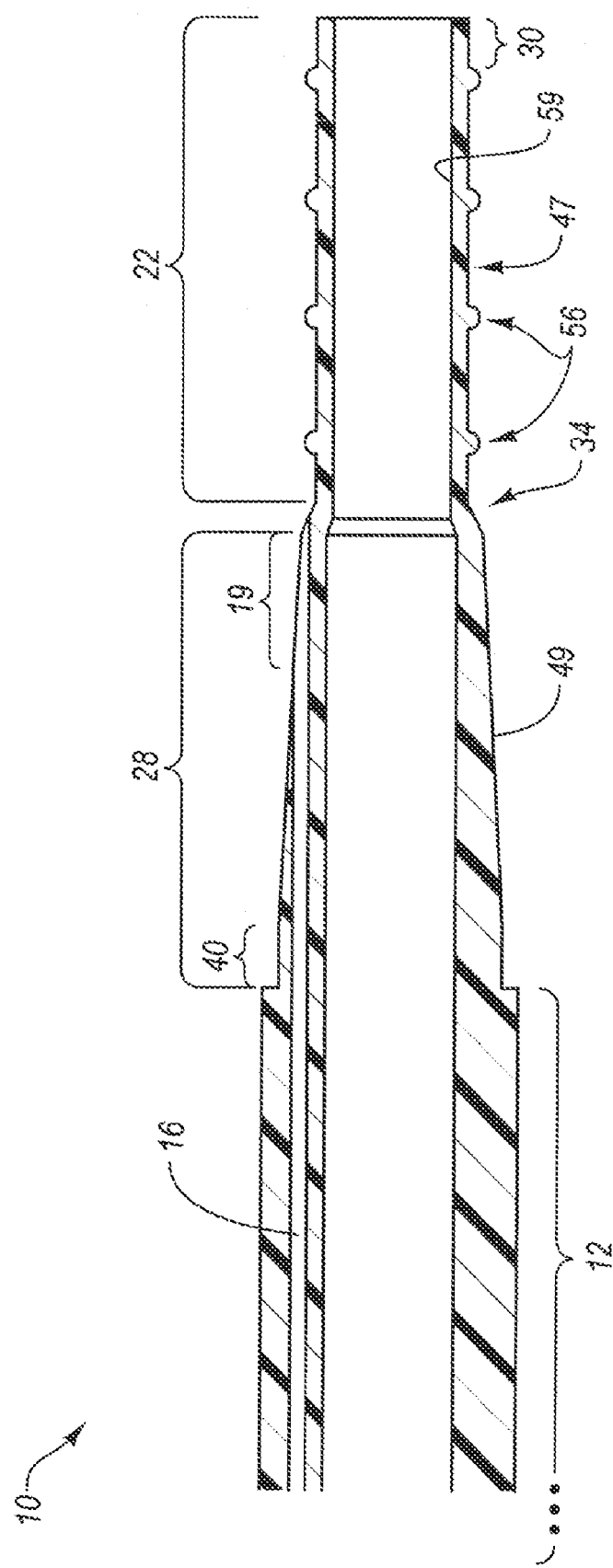
FIG. 5B is an enlarged cross-sectional side view of an exemplary feeding tube device according to an additional embodiment.

FIG. 5B is an enlarged cross-sectional side view of an exemplary feeding tube device 10 according to an additional embodiment. As seen in this figure, exemplary feeding tube device 10 may comprise a substantially cylindrical body region 12, a tip region 28 extending longitudinally from body region 12, and an overlapping segment 22 extending longitudinally from tip region 28. Feeding tube device 10 may also comprise one or more rib structures 56 provided on the exterior surface 47 of overlapping segment 22, an interior surface 59 of overlapping segment 22, or both, without limitation. In certain embodiments, rib structures 56 may help to reinforce or generate a desired shape of a balloon structure (such as, for example, balloon structure 70) formed upon inflation of overlapping segment 22, as detailed above.

As detailed above, the size, shape, or position of each of the various balloon structure embodiments described and/or illustrated herein may be modified as desired. In addition, as opposed to comprising a pliant material, an overlapping segment for forming a balloon structure may comprise a relatively non-pliant material, such as a polymer. Examples of suitable non-pliant polymers include, without limitation, polyethylene terephthalate (PET), polyurethane, polyethylene (PE), nylon, polyvinyl chloride (PVC), or any other suitable material. In certain embodiments, the material or combination of materials used to form the overlapping segment of the feeding tube device may allow for a balloon structure formed by inflating or expanding the overlapping segment to retain relatively high pressures. For example, a balloon structure formed of relatively non-pliant material may retain a desired size and shape even under high pressure, in comparison to balloon structures comprising relatively pliant materials. In addition, these so-called high-pressure balloon structures may be relatively thin-walled and may exhibit relatively high tensile strength with relatively low elongation. Such high-pressure balloon structures may also have relatively high chemical resistance properties. Accordingly, high-pressure balloon structures with thinner walls, higher strength, higher chemical resistance properties, and/or smaller profiles may be advantageously suited for use in a feeding tube device, such as exemplary feeding device 10. In some embodiments, the low profile of these exemplary balloon structures may permit the feeding tube device to be percutaneously placed within a patient through a sheath or introducer.

In at least one embodiment, one or more of the exemplary feeding tube devices described and/or illustrated herein may be structured so that at least partial expansion of the balloon structure does not depend on changing the shape or size of the material forming the overlapping segment. Rather, an overlapping segment may be structured with folds or pleats so that expansion of the overlapping segment may occur without significant deformation of the overlapping segment. In certain embodiments, these folds or pleats may be wrapped or otherwise folded or compressed around the tip region of the feeding tube device prior to insertion within a stomach of a patient.

Figure 6A:
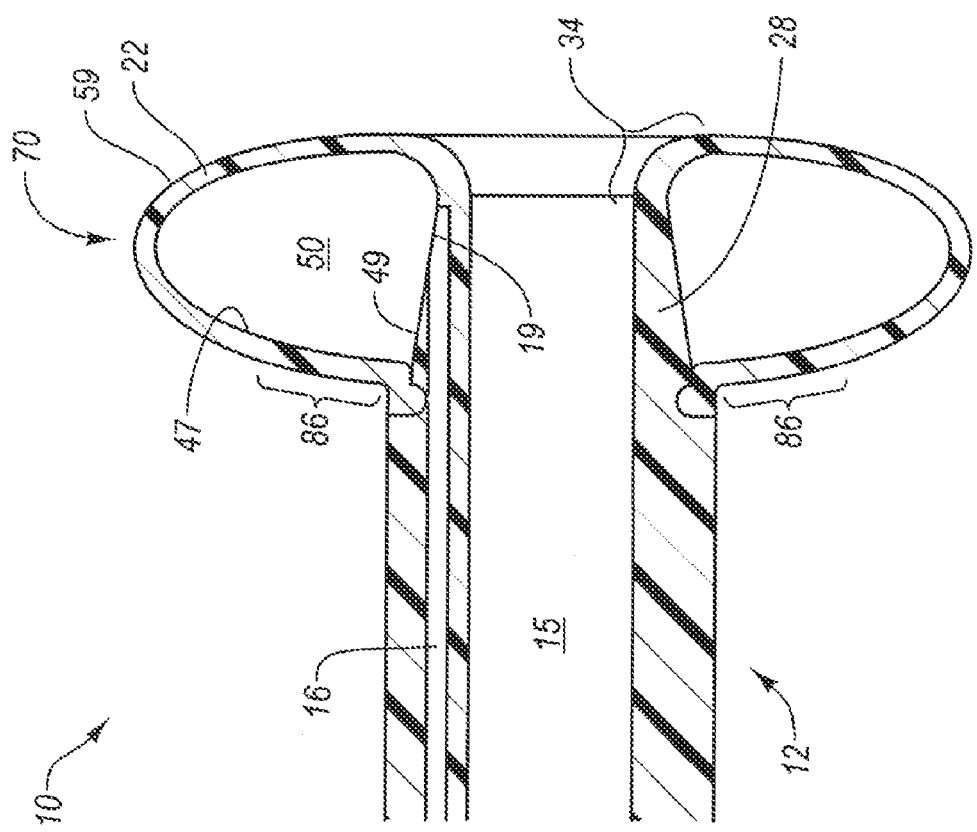
FIG. 6A is a schematic cross-sectional side view of an exemplary feeding tube device according to an additional embodiment.
Figure 6C:
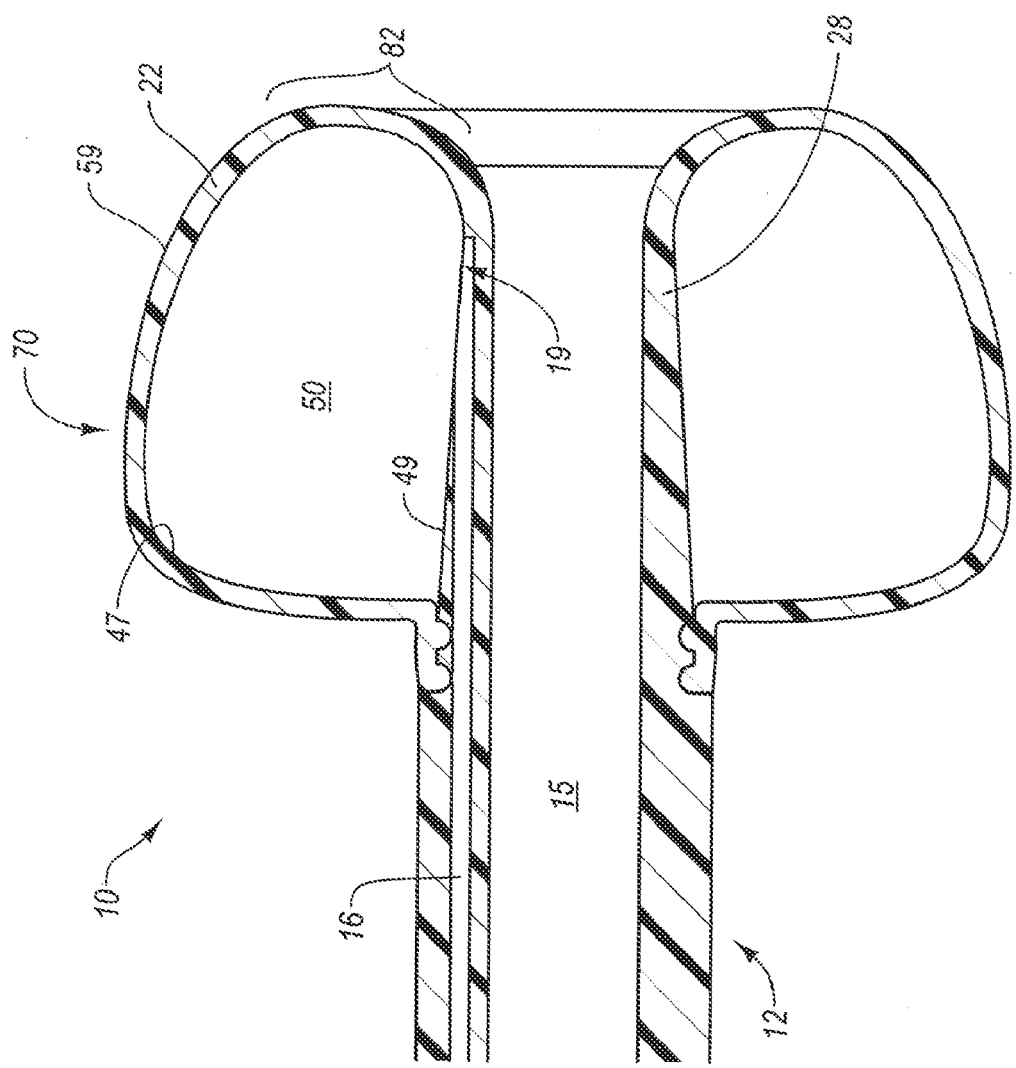
FIG. 6C is a schematic cross-sectional side view of an exemplary feeding tube device according to an additional embodiment.

As detailed above, balloon structure 70 may be formed in a variety of lengths, cross-sectional shapes, and sizes. For example, as illustrated in the cross-sectional side view of FIG. 6A, a balloon structure 70 may be formed in a "low profile" disk-like shape comprising a transverse portion 86 having ample surface area for engaging against a stomach wall. In addition, as illustrated in the cross-sectional side view of FIG. 6B, balloon structure 70 may be substantially "D" shaped and comprise a transverse portion 86 that extends from body region 12 substantially perpendicularly, with overlapping segment 22 extending along a generally arcuate path. Moreover, as illustrated in the cross-sectional side view of FIG. 6C, balloon structure 70 may be substantially "B" shaped and comprise a gradual, rounded end region 82, which may be beneficial for preventing trauma to a stomach.

Figure 7:
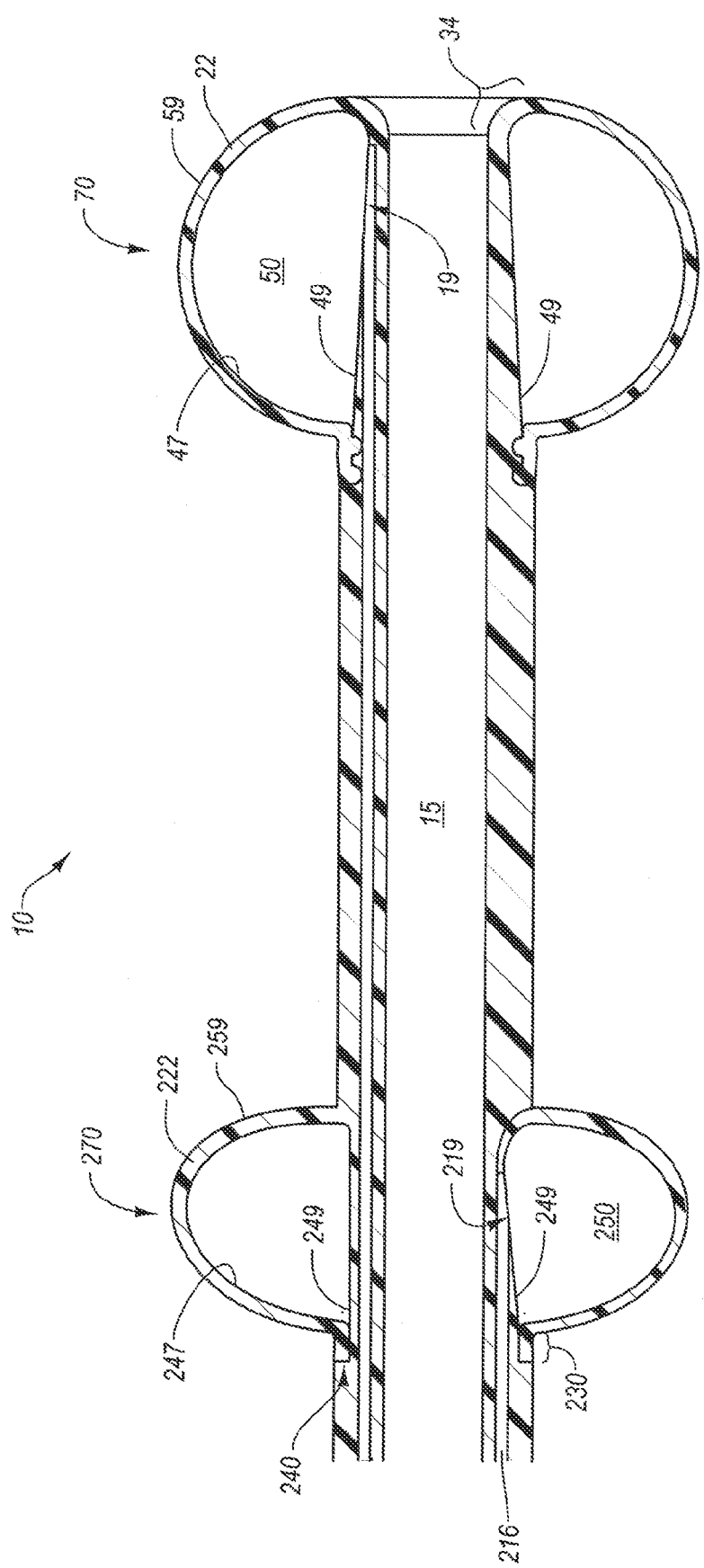
FIG. 7 is a schematic cross-sectional side view of an exemplary feeding tube device according to an additional embodiment.

FIG. 7 is a schematic cross-sectional side view of an exemplary feeding tube device 10 according to an additional embodiment. As seen in this figure, feeding tube device 10 may comprise a substantially cylindrical body region 12, a tip region 28 extending longitudinally from body region 12, and an overlapping segment 22 extending longitudinally from tip region 28. In certain embodiments, feeding tube device 10 may also comprise an overlapping segment 222 integrally formed with and extending from the proximate end of body region 12 of feeding tube device 10. As with overlapping segment 22, overlapping segment 222 may be folded backwards and disposed or positioned over and around at least a portion of body region 12. In certain embodiments, an exterior surface 247 of overlapping segment 222 may comprise a sealing surface 230 that may be adhered, bonded, or otherwise affixed to a receiving surface 240 provided on the exterior surface 249 of body region 12. As with sealing surface 30 and receiving surface 40, sealing surface 230 and receiving surface 240 may be formed in any number of shapes and sizes. For example, sealing surface 230 and receiving surface 240 may respectively comprise a plurality of coupling structures and coupling recesses or may be substantially cylindrical in shape.

In at least one embodiment, a chamber 250 may be formed between the exterior surface 247 of overlapping segment 222 and the exterior surface 249 of body region 12 by melting, adhering, bonding, sealing, or otherwise affixing at least a portion of sealing surface 230 of overlapping segment 222 to receiving surface 240 of body region 12. As seen in FIG. 7, chamber 250 may be in communication (e.g., pneumatic or hydraulic communication) with an aperture 219 and an inflation lumen 216 defined within body region 12. In certain embodiments, a proximal balloon structure 270 may be formed proximate a proximal end of feeding tube device 10 by expanding at least a portion of overlapping segment 222 by communicating a fluid or gas through inflation lumen 216, out aperture 219, and into chamber 250. Similarly, a distal balloon structure 70 may be formed proximate a distal end of feeding tube device 10 by expanding at least a portion of overlapping segment 22 by communicating a fluid or gas through inflation lumen 16, out aperture 19 and into chamber 50. Distal balloon structure 70 and proximal balloon structure 270 may be formed in any number of shapes and sizes and may be formed of any number or combination of materials.

In at least one embodiment, distal balloon structure 70 may be positioned within a patient's stomach and proximal balloon structure 270 may be positioned proximate to the exterior skin surface of the patient to retain or hold at least a portion of feeding tube device 10 within the patient. In other words, the abdominal and stomach walls of a patient may be sandwiched between distal balloon structure 70 and proximal balloon structure 270 to help retain exemplary feeding device 10 in a preferred position.

It is desired that the embodiments described herein be considered in all respects illustrative and not restrictive and that reference be made to the appended claims and their equivalents for determining the scope of the instant disclosure. For ease of use, the words "including" and "having," as used in the specification and claims, are interchangeable with and have the same meaning as the word "comprising."

What is claimed is:

1. A feeding tube device for delivering a substance into a stomach of a patient, comprising:
   a feeding tube including a central feeding lumen having a circular cross-sectional shape from a proximate end to a distal end; and
   an overlapping segment integrally formed with and extending from the distal end of the feeding tube, the overlapping segment surrounding a tip region of the feeding tube to form a balloon structure in fluid communication with an inflation lumen, wherein a junction of the feeding tube and the overlapping segment forms a smooth outer surface having a constant diameter.

2. The feeding tube device according to claim 1, wherein the balloon structure, following inflation, includes a transverse portion extending substantially perpendicularly with respect to an outer surface of the feeding tube.

3. The feeding tube device according to claim 2, wherein the overlapping segment, following inflation, extends along a generally arcuate path.

4. The feeding tube device according to claim 1, wherein the tip region of the feeding tube is substantially frustoconical in shape.

5. The feeding tube device according to claim 1, wherein the balloon structure extends beyond the distal end of the feeding tube device when the balloon structure is inflated.

6. The feeding tube device according to claim 1, wherein the overlapping segment is formed of a substantially non-pliant material.

7. The feeding tube device according to claim 6, wherein the substantially non-pliant material is polyethylene terephthalate.

8. A feeding tube device for delivering a substance into a stomach of a patient, comprising:
   a feeding tube including a proximate end and a distal end; and
   an overlapping segment integrally formed with and extending from the distal end of the feeding tube, the overlapping segment surrounding a tip region of the feeding tube to form a balloon structure in fluid communication with an inflation lumen, wherein the junction of the feeding tube and the overlapping segment form a smooth outer surface having a constant diameter.

9. The feeding tube device according to claim 8, wherein the feeding tube includes a circular cross-sectional shape from a proximate end to a distal end.

10. The feeding tube device according to claim 8, wherein the balloon structure, following inflation, includes a transverse portion extending substantially perpendicularly with respect to an outer surface of the feeding tube.

11. The feeding tube device according to claim 10, wherein the overlapping segment, following inflation, extends along a generally arcuate path.

12. The feeding tube device according to claim 8, wherein the overlapping segment has a constant cross-section.

13. The feeding tube device according to claim 12, wherein the overlapping segment includes one or more rib structures on an exterior surface thereof.

14. A feeding tube device for delivering a substance into a stomach of a patient, comprising:
   a feeding tube including a proximate end and a distal end; and
   an overlapping segment integrally formed with and extending from the distal end of the feeding tube, the overlapping segment surrounding a tip region of the feeding tube to form a balloon structure in fluid communication with an inflation lumen, wherein a junction of the feeding tube and the overlapping segment forms a smooth outer surface having a constant diameter, and wherein the balloon structure, following inflation, includes a transverse portion extending substantially perpendicularly with respect to an outer surface of the feeding tube.

15. The feeding tube device according to claim 14, wherein the overlapping segment, following inflation, extends along a generally arcuate path.

16. The feeding tube device according to claim 15, wherein the overlapping segment, following inflation, is substantially "D" shaped.

17. The feeding tube device according to claim 16, wherein the feeding tube includes a circular cross-sectional shape from a proximate end to a distal end.

18. The feeding tube device according to claim 17, wherein the overlapping segment is formed of a substantially non-pliant material.

* * * * *